(12) United States Patent
Myoung (10) Patent No.: US 11,727,791 B2
(45) Date of Patent: Aug. 15, 2023

(54) CANDLE WARMER HAVING MOBILE COMMUNICATION AND EXTERNAL INTERFACE FUNCTION

(71) Applicant: HYUNPEOPLE CO., LTD, Guri-si (KR)

(72) Inventor: Soo Hyun Myoung, Seoul (KR)

(73) Assignee: HYUNPEOPLE CO., LTD, Guri-si (KR)

( * ) Notice: Subject to any disclaimer, the term of this patent is extended or adjusted under 35 U.S.C. 154(b) by 59 days.

(21) Appl. No.: 17/607,095

(22) PCT Filed: Jun. 17, 2019

(86) PCT No.: PCT/KR2019/007247
§ 371 (c)(1),
(2) Date: Oct. 28, 2021

(87) PCT Pub. No.: WO2020/222353
PCT Pub. Date: May 11, 2020

(65) Prior Publication Data
US 2022/0230532 A1    Jul. 21, 2022

(30) Foreign Application Priority Data
Apr. 29, 2019 (KR) .......... 10-2019-0049509

(51) Int. Cl.
*G08C 17/02* (2006.01)
*H05B 1/02* (2006.01)
*H05B 3/00* (2006.01)

(52) U.S. Cl.
CPC .......... *G08C 17/02* (2013.01); *H05B 1/0252* (2013.01); *H05B 3/0071* (2013.01); *G08C 2201/30* (2013.01); *G08C 2201/51* (2013.01); *G08C 2201/93* (2013.01)

(58) Field of Classification Search
CPC .......... G08C 17/02; G08C 2201/30; G08C 2201/51; H05B 1/0252; F21S 6/001; F23Q 25/00
See application file for complete search history.

(56) References Cited

U.S. PATENT DOCUMENTS

| 2011/0244406 A1* | 10/2011 | Simpson | F23N 5/203 |
| | | | 431/6 |
| 2017/0097157 A1* | 4/2017 | Simpson | F23Q 25/00 |
| 2018/0072965 A1* | 3/2018 | Han | F23Q 25/00 |

FOREIGN PATENT DOCUMENTS

| KR | 10-0773750 B1 | 11/2007 |
| KR | 10-2012-0091735 A | 8/2012 |
| KR | 10-2018-0013313 A | 2/2018 |
| KR | 10-2018-0017602 A | 2/2018 |
| KR | 10-2018-0132427 A | 12/2018 |

* cited by examiner

*Primary Examiner* — Vernal U Brown
(74) *Attorney, Agent, or Firm* — Bridgeway IP Law Group, PLLC; Sang Ho Lee; Hyun Woo Shin (57) ABSTRACT

Provided is a candle warmer having mobile communication and external interface functions, and more specifically, to a candle warmer having mobile communication and external interface functions, which prevents malfunction of the candle warmer in advance by setting operation information of the candle warmer in advance, is monitored through a smart device to realize an operation selected by a user and includes a remote controller interface function to improve user convenience.

10 Claims, 6 Drawing Sheets

| MODE | OPERATION START TIME | OPERATION END TIME | THRESHOLD TEMPERATURE | AMBIENT TEMPERATURE |
|---|---|---|---|---|
| AWAY | | | | |
| MORNING | | | | |
| AFTERNOON | | | | |
| EVENING | | | | |
| SLEEP | | | | |

FIG. 11

CANDLE WARMER HAVING MOBILE COMMUNICATION AND EXTERNAL INTERFACE FUNCTION

TECHNICAL FIELD

The present disclosure relates to a candle warmer having mobile communication and external interface functions, and more specifically, to a candle warmer having mobile communication and external interface functions, which is capable of preventing malfunction thereof in advance by setting operation information thereof in advance, is monitorable through a smart device to implement an operation selected by a user, and has a remote controller interface function to improve user convenience.

BACKGROUND ART

In general, a candle warmer is a scent-emitting device that emits light to a fragrant candle containing a fragrant substance, such as an aroma, using a light source generating high-temperature heat, e.g., a halogen lamp, and melts the fragrant candle using heat generated from the emitted light to diffuse the fragrant substance into the air.

Although a fragrant candle may be burnt to emit a scent, carcinogenic chemicals such as formaldehyde may be generated, and thus, recently, a method of melting a candle using a candle warmer has been widely used to prevent in advance an oxygen deficit, generation of hazardous compounds when a candle is burnt, a headache due to carbon monoxide, etc.

In general, a candle warmer includes a main body configured to place a candle on a side thereof, a lamp provided at a position corresponding to an upper part of the candle to emit light with heat, a socket which supplies power to the lamp, a lampshade provided to surround the lamp and the socket to concentrate light and heat emitted from the lamp, a supporter configured to fasten the socket into the lampshade, and an extension tube extending from another side of the main body such that the supporter is located at a certain height.

The candle warmer heats an entire upper surface of a fragrant candle to vaporize the fragrant candle, thereby emitting a scent. However, when the upper surface of the fragrant candle is heated, a strong scent is emitted but gradually fades because perfume contained in the upper surface becomes consumed as time goes by.

Furthermore, when the height of the fragrant candle gradually reduces due to the vaporization of the fragrant candle, the distance between the fragrant candle and the lamp increases and thus the amount of heat applied to the fragrant candle reduces, thus greatly reducing the effect of emitting a scent, and as heat is continuously applied to the fragrant candle, the fragrant candle is chemically deformed by heat, thus causing melting or deforming of a container of the fragrant candle.

In addition, when a user is asleep, the candle warmer cannot be safely used because the candle warmer is continuously heated while the fragrant candle is heated to emit the scent.

PRIOR ART LITERATURE

Patent Document (Patent Document 1) Korean patent application No. 10-2016-0096841 (filed on Jul. 29, 2016, entitled "Candle Warmer Having Function of Wireless Communication and Internet of Things")

DISCLOSURE

Technical Problem

To address the above problems, the present disclosure is directed to providing a candle warmer having mobile communication and external interface functions, in which a remote control is provided to remotely control the candle warmer by a user of the candle warmer and a user terminal belonging to the user and having an external communication function, thereby providing convenience of use and managing usage information.

The present disclosure is also directed to providing a candle warmer having mobile communication and external interface functions, in which an operational state and operation information may be easily collected and managed by a temperature sensor for detecting temperature information and transmitting collected temperature information to a candle controller and a power sensor for detecting whether an external power source is applied.

The present disclosure is also directed to providing a candle warmer having mobile communication and external interface functions, in which an accident due to overheating may be prevented by management through a user terminal processor configured to communicate with a user terminal and collect temperature information collected by a temperature sensor and power information collected by a power sensor by requesting the candle controller to provide the temperature information and the power information.

The present disclosure is also directed to providing a candle warmer having mobile communication and external interface functions, in which operation information is monitored by storing, in a database, a threshold operation time of the candle warmer, a threshold temperature, the temperature information collected by the candle controller, heating lamp operation start date and time, heating lamp operation end date and time, and power supply information.

The present disclosure is also directed to providing a candle warmer having mobile communication and external interface functions, in which setting information additionally includes information about various types of operation modes, including an away mode, a morning mode, an afternoon mode, an evening mode, and a sleep mode, and thus, a heating time of a heating lamp and a heating time may be controlled on the basis of the various types of operation mode information.

The present disclosure is also directed to providing a candle warmer having mobile communication and external interface functions, in which a remote control includes a remote control inputter, a remote control signal converter and a remote control signal transmitter, and thus, information input to the remote control inputter is converted into a transmission signal by the remote control signal converter and the transmission signal is transmitted through the remote control signal transmitter and received by a remote control receiver, thereby increasing user convenience and operation stability.

Technical aspects of the present disclosure are not limited thereto, and other aspects that are not mentioned herein will be clearly understood by those of ordinary skill in the art to which the present disclosure pertains from the following description.

Technical Solution

According to an aspect of the present disclosure, a candle warmer having mobile communication and external interface functions includes a user terminal (100) belonging to a user of the candle warmer and capable of communicating with external devices.

Here, the candle warmer may include a remote control (200) configured to interface with the candle warmer to allow the user to operate the candle warmer.

The candle warmer may include a candle controller (300) including a communicator (310) configured to connect to the user terminal (100), a remote control receiver (320) configured to interface with the remote control (200), and an internal timer (330).

In this case, the candle warmer may include a temperature sensor (400) configured to detect temperature information and transmit collected temperature information to the candle controller (300).

The candle warmer may include a power sensor (500) configured to be connected to the candle controller (300) so as to detect whether an external power source is applied.

Here, the candle warmer may include a user terminal processor (600) configured to communicate with the user terminal (100) and request the candle controller (300) to transmit temperature information collected by the temperature sensor (400) and power information collected by the power sensor (500) so as to collect the temperature information and the power information.

In this case, the user terminal processor (600) may include: a database (610) storing operation information (610a), including at least a candle warmer operation threshold time, a threshold temperature, the temperature information collected by the candle controller (300), heating lamp operation start date and time, heating lamp operation end date and time, and power supply information; a display (620); and an input means (630).

Here, the user terminal processor (600) may display details of operating the candle warmer (W) on the display (620) on the basis of the operation information (610a) stored in the database (610) and according to a condition input by a user through the input means (630).

In addition, the user terminal processor (600) may receive setting information (631) through the input means (630) and store the setting information (631) in the database (610) so as to control a lamp operation time according to the temperature information collected by the temperature sensor (400), transmit the setting information (631) to the candle controller (300) to be stored in the memory (340), and synchronize the database (610) and the memory (340) with each other at a certain time interval.

The setting information (631) may further include information about operation modes, including at least an away mode (631a), a morning mode (631b), an afternoon mode (631c), an evening mode (631d), and a sleep mode (631e), and the candle controller (330) may control a heating time of a heating lamp and a heating time on the basis of time information collected by the internal timer (330) and the information about the operation modes stored in the memory (340).

Here, the remote control (200) may further include a remote control inputter (210), a remote control signal converter (220), and a remote control signal transmitter (230), and information input to the remote control inputter (210) may be converted into a transmission signal by the remote control signal converter (220), and the transmission signal may be transmitted through the remote control signal transmitter (230) and received by the remote control receiver (320).

In this case, the remote control inputter (210) may include an input button on a front surface of a casing of the remote control (200), and the input button may include at least a power button (210a), an illumination button (210b) and a time button (210c). When the input button is pressed, the remote control signal converter (220) may form a digital signal corresponding to the remote control inputter (210), and the remote control signal transmitter (230) may transmit the digital signal. When the digital signal is received by the remote control receiver (320), the candle controller (330) may ignore the setting information (631) and preferentially control the digital signal.

The candle controller (300) may turn off a power source immediately when a temperature collected by the temperature sensor (400) is greater than or equal to a threshold temperature stored in the memory (340) and a state detected by the power sensor (500) is a power supply state, and transmit the temperature and the threshold temperature to the user terminal processor (600) through the communicator (310), and the user terminal processor (600) may display the temperature and the threshold temperature transmitted thereto on the display (620).

The candle controller (300) may store operation time in the memory (340) using the internal timer (330) immediately after the candle warmer W is turned on, compare the operation time stored in the memory (340) with a set threshold time at certain time intervals, control a power source to be turned off immediately when a total operation time exceeds the threshold time, and transmit information about collected temperatures, the threshold temperature, and the threshold time to the user terminal processor (600) through the communicator (310) when the power source is turned off, and the user terminal processor (600) may display the received information on the display (620).

In this case, the user terminal processor (600) may receive information about a lamp lifespan, for exchanging heating lamps, through the input means (630), store the information about the lamp lifespan in the database (610), and display a lamp exchange message and a total lamp operation time on the display (620) when the lamp lifespan is over.

In addition, the user terminal processor (600) may store information about output sound corresponding to the operation information (610a) in the database (610) and output the information about the output sound on the basis of the operation information (610a) received from the candle controller (300), when the information about the output sound is input to the user terminal processor (600) or is selected through the input means (630), and the output sound may be stored in the user terminal (100) or provided to interface with an external system or an external server.

Advantageous Effects

Accordingly, the present disclosure provides a candle warmer having mobile communication and external interface functions to achieve the following effects.

First, the candle warmer is provided with a remote control to remotely control the candle warmer by a user of the candle warmer and a user terminal belonging to the user and having an external communication function, thereby providing convenience of use and managing usage information.

Second, a temperature sensor configured to detect temperature information and transmit collected temperature information to a candle controller and a power sensor configured to detect whether an external power source is applied are used to provide convenience in collecting and managing an operational state and operation information.

Third, a user terminal processor is used to communicate with the user terminal and collect temperature information collected by a temperature sensor and power information collected by a power sensor by requesting a candle controller to provide the temperature information and the power information, thereby preventing an accident due to excessive heating.

Fourth, operation information can be monitored by storing, in a database, a threshold operation time of the candle warmer, a threshold temperature, the temperature information collected by the candle controller, heating lamp operation start date and time, heating lamp operation end date and time, and power supply information.

Fifth, setting information additionally includes information about various types of operation modes, including an away mode, a morning mode, an afternoon mode, an evening mode, and a sleep mode, and thus, a heating time of a heating lamp and a heating time can be conveniently controlled on the basis of the various types of operation mode information.

Sixth, the remote control includes a remote control inputter, a remote control signal converter, and a remote control signal transmitter, and thus, information input to the remote control inputter is converted into a transmission signal by the remote control signal converter and the transmission signal is transmitted through the remote control signal transmitter and received by a remote control receiver, thereby increasing user convenience and operation stability.

Effects of the present disclosure are not limited thereto, and other effects that are not mentioned herein will be clearly understood by those of ordinary skill in the art to which the present disclosure pertains from the following description.

DESCRIPTION OF DRAWINGS

The following drawings appended herein illustrate examples of an embodiment of the present disclosure and are provided to help understand the technical idea of the present disclosure together with the detailed description and thus the present disclosure should not be interpreted as being limited thereto.

MODES OF THE INVENTION

A description of specific structures or functions of embodiments according to the concept of the present disclosure set forth herein is provided merely to describe the embodiments according to the concept of the present disclosure and thus embodiments according to the concept of the present disclosure may be implemented in various forms and are not limited the embodiments described herein.

Various modifications may be made in embodiments according to the concept of the present disclosure and these embodiments may be implemented in various forms and thus embodiments are illustrated in the drawings and described in detail in the present specification. However, embodiments according to the concept of the present disclosure are not limited to specific forms and should be understood to include all modifications, equivalents, or alternatives included in the spirit and technical scope of the present disclosure.

Figure 1:
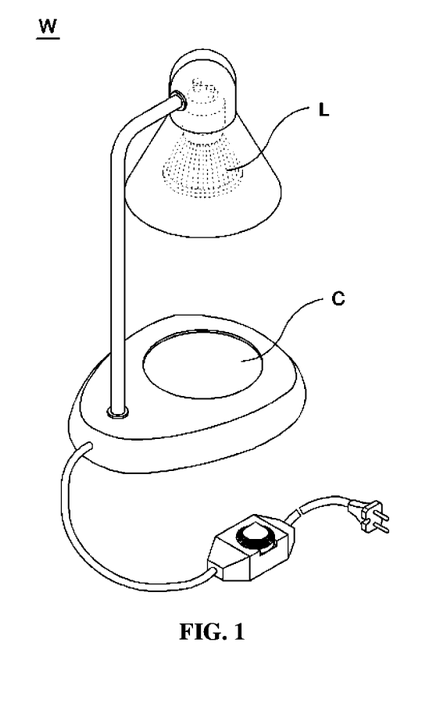
FIG. 1 is a perspective view of a candle warmer having mobile communication and external interface functions according to an embodiment of the present disclosure.
Figure 2:
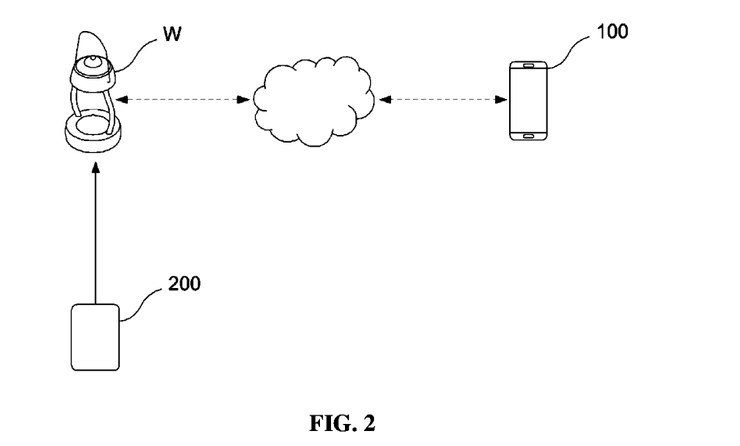
FIGS. 2 and 3 are a system configuration diagram and a system flow conceptual diagram for describing interfacing of a candle warmer having mobile communication and external interface functions according to an embodiment of the present disclosure.
Figure 3:
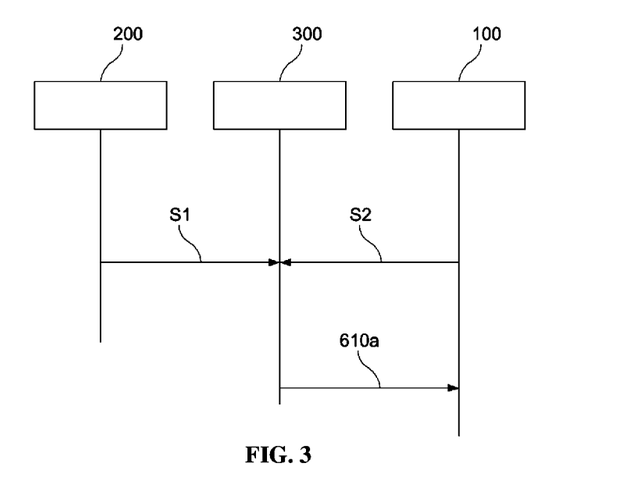
Figure 4:
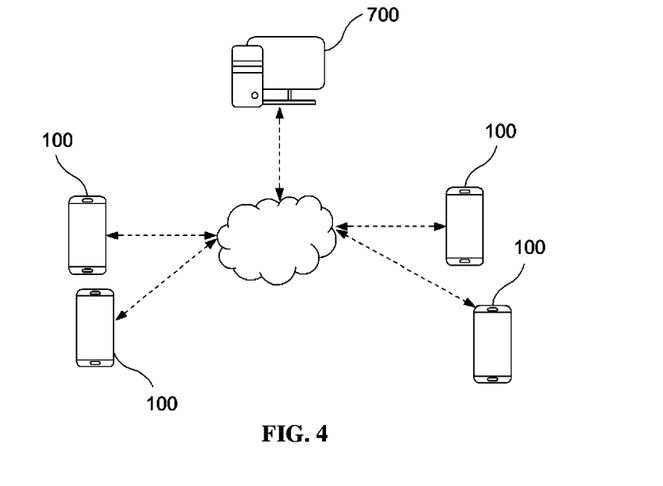
FIGS. 4 and 5 are a system configuration diagram and a system flow conceptual diagram for describing interfacing between an external server and a candle warmer having mobile communication and external interface functions according to an embodiment of the present disclosure.
Figure 5:
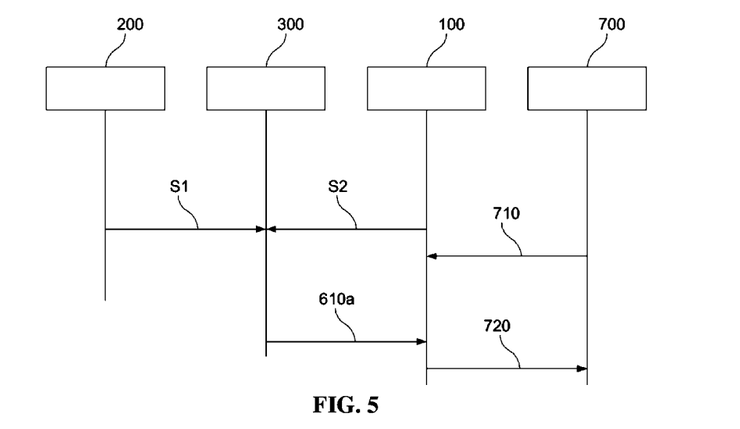
Figure 6:
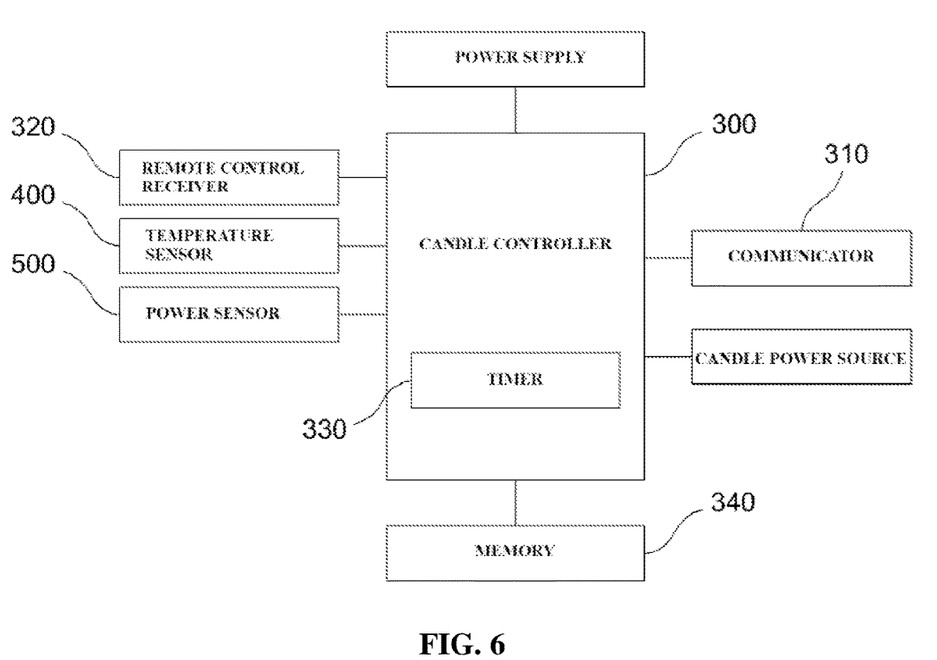
FIG. 6 is a block diagram of a candle controller of a candle warmer having mobile communication and external interface functions according to an embodiment of the present disclosure.
Figure 7:
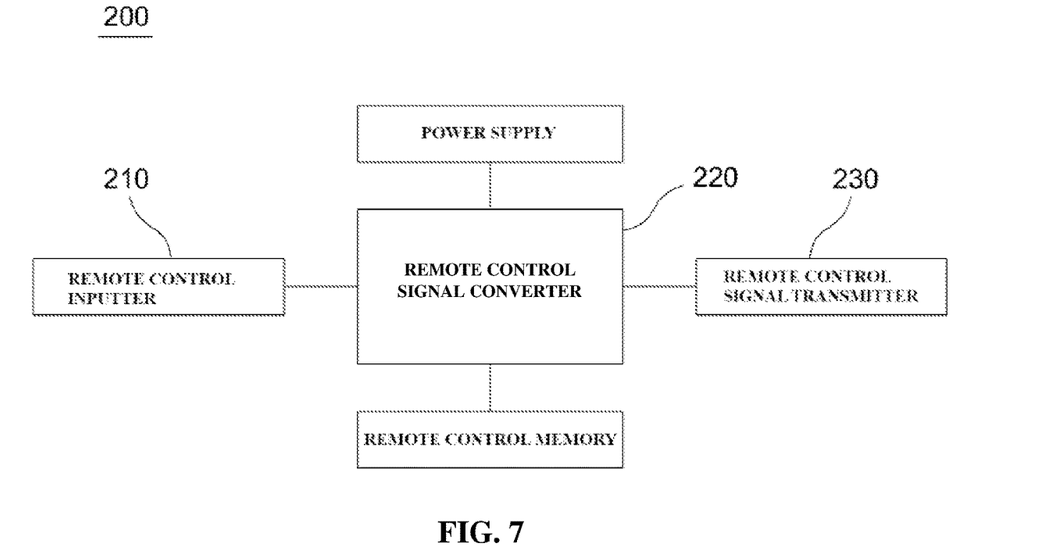
FIGS. 7 and 8 are a block diagram and a conceptual diagram of a remote control of a candle warmer having mobile communication and external interface functions according to an embodiment of the present disclosure.
Figure 8:
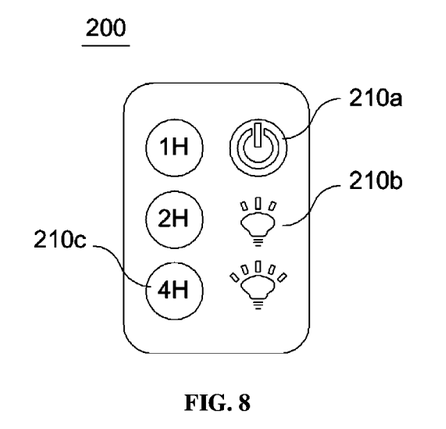
Figure 9:
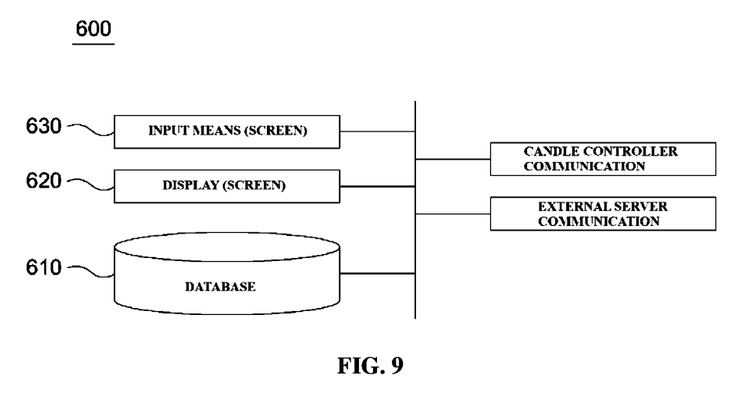
FIGS. 9 to 11 are a conceptual diagram and diagrams for describing a user terminal processor of a candle warmer having mobile communication and external interface functions according to an embodiment of the present disclosure.
Figure 10:
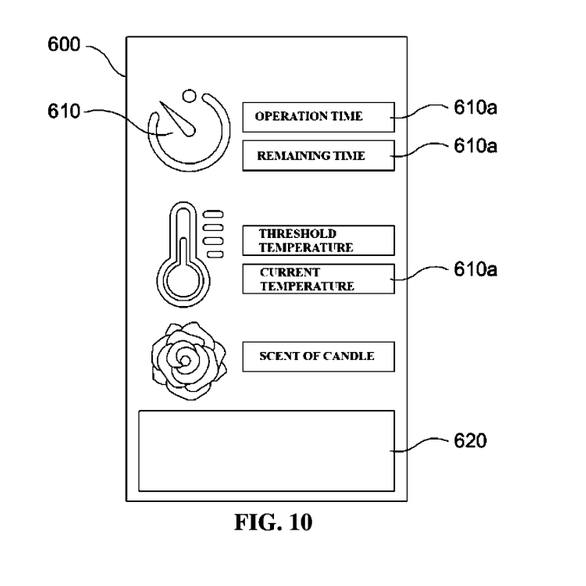
Figure 11:
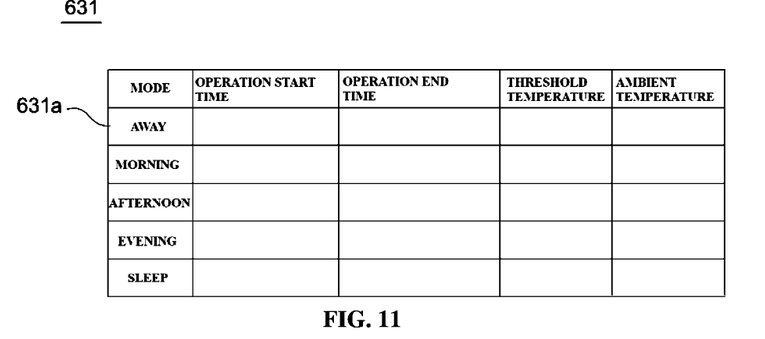

FIG. 1 is a perspective view of a candle warmer having mobile communication and external interface functions according to an embodiment of the present disclosure. FIGS. 2 and 3 are a system configuration diagram and a system flow conceptual diagram for describing interfacing of a candle warmer having mobile communication and external interface functions according to an embodiment of the present disclosure. FIGS. 4 and 5 are a system configuration diagram and a system flow conceptual diagram for describing interfacing between an external server and a candle warmer having mobile communication and external interface functions according to an embodiment of the present disclosure. FIG. 6 is a block diagram of a candle controller of a candle warmer having mobile communication and external interface functions according to an embodiment of the present disclosure. FIGS. 7 and 8 are a block diagram and a conceptual diagram of a remote control of a candle warmer having mobile communication and external interface functions according to an embodiment of the present disclosure. FIGS. 9 to 11 are a conceptual diagram and diagrams for describing a user terminal processor of a candle warmer having mobile communication and external interface functions according to an embodiment of the present disclosure.

As illustrated in FIG. 1, a candle warmer W having mobile communication and external interface functions according to an embodiment of the present disclosure includes a heating lamp L and a candle mounting part C which is provided immediately below the heating lamp L and on which a candle containing a fragrant material is placed.

Here, a user terminal 100 belonging to a user of the candle warmer W and having an external communication function is provided.

That is, as shown in FIG. 2, the candle warmer W and the user terminal 100 each include a communication module therein and thus may be connected to each other through wireless communication.

A remote control 200 is configured to interface with the candle warmer W to allow the user to operate the candle warmer W.

Here, as shown in FIG. 3, the candle warmer W may interface with or be communicatively connected to the remote control 200 and the user terminal 100 using a candle controller 300 included or mounted in the candle warmer W.

That is, the candle warmer W is operated using a remote control signal S1 transmitted from the remote control 200 and a user signal S2 transmitted from the user terminal 100.

In this case, the candle controller 300 includes a communicator 310 configured to connect to the user terminal 100, a remote control receiver 320 configured to interface with the remote control 200, and an internal timer 330.

As shown in FIGS. 4 to 5, the user terminal 100 may be connected to an external server 700 to transmit information to the external server 700 and receive data from the external server 700 and transmit the data to the candle warmer W to control an operation of the candle warmer W.

The candle warmer W includes a temperature sensor 400 to detect temperature information and transmit collected temperature information to the candle controller 300.

The candle warmer W further includes a power sensor 500 to be connected to the candle controller 300 so as to detect whether an external power is applied and transmit a detection result to the user terminal 100 or the external server 700 through the candle controller 300 as illustrated in FIG. 6.

Here, as illustrated in FIG. 9, a user terminal processor 600 is provided to communicate with the user terminal 100 and request the candle controller 300 to transmit temperature information collected by the temperature sensor 400 and power information collected by the power sensor 500 so as to collect the temperature information and the power information.

In this case, as shown in FIG. 10, the user terminal processor 600 includes: a database 610 storing operation information 610a including at least a candle warmer operation threshold time, a threshold temperature, temperature information collected by the candle controller 300, heating lamp operation start date and time, heating lamp operation end date and time, and power supply information; a display 620; and an input means 630.

Here, the user terminal processor 600 displays details of operating the candle warmer W on the display 620 on the basis of the operation information 610a stored in the database 610 and according to a result of searching for a condition input by a user through the input means 630.

In this case, at least an image, a moving image, and text is displayed on the display 620.

The user terminal processor 600 may receive setting information 631 through the input means 630 to be stored in the database 610 so as to control a lamp operation time according to the temperature information collected by the temperature sensor 400, the setting information 631 may be transmitted to the candle controller (300) to be stored in the memory (340), and the database (610) and the memory (340) may be synchronized with each other at a certain time interval.

Here, the setting information 631 may further include information about operation modes, including at least an away mode 631a, a morning mode 631b, an afternoon mode 631c, an evening mode 631d, and a sleep mode 631e, as illustrated in FIG. 11. The candle controller 330 may control a heating time of a heating lamp and a heating time on the basis of time information collected by the internal timer 330 and the information about the operations modes stored in the memory 340. The setting information 631 may be distributed to the candle warmer W via the user terminal 100 through the external server 700.

As illustrated in FIGS. 7 and 8, the remote control 200 may include a remote control inputter 210, a remote control signal converter 220, and a remote control signal transmitter 230, and information input to the remote control inputter 210 may be converted into a transmission signal by the remote control signal converter 220 and the transmission signal may be transmitted through the remote control signal transmitter 230 and received by the remote control receiver 320.

In this case, the remote control signal converter 220 may map an output signal corresponding to the input information by storing the output signal in advance in a memory or may generate the output signal through a remote control circuit.

In this case, the remote control inputter 210 may include an input button on a front surface of a casing of the remote control 200. The input button may include at least a power button 210a, an illumination button 210b and a time button 210c. When the input button is pressed, the remote control signal converter 220 may form a digital signal corresponding to the remote control inputter 210 and the remote control signal transmitter 230 may transmit the digital signal. When the digital signal is received by the remote control receiver 320, the candle controller 330 may ignore the setting information 631 and preferentially control the digital signal.

Here, the candle controller 300 may turn off a power source immediately when a temperature collected by the temperature sensor 400 is greater than or equal to a threshold temperature stored in the memory 340 and a state detected by the power sensor 500 is a power supply state, and transmit the temperature and the threshold temperature to the user terminal processor 600 through the communicator 310, and the user terminal processor 600 may display the temperature and the threshold temperature transmitted thereto on the display 620 as illustrated in FIG. 10.

The candle controller 300 may store operation time in the memory 340 using the internal timer 330 immediately after the candle warmer W is turned on, compare the operation time stored in the memory 340 with a set threshold time at certain time intervals, control a power source to be turned off immediately when a total operation time exceeds the threshold time, and transmit information about collected temperatures, the threshold temperature, and the threshold time to the user terminal processor 600 through the communicator 310 when the power source is turned off, and the user terminal processor 600 may display the received information on the display 620.

The user terminal processor 600 may receive information about a lamp lifespan, for exchanging heating lamps, through the input means 630, store the information about the lamp lifespan in the database 610, and display a lamp exchange message and a total lamp operation time on the display 620 when the lamp lifespan is over.

The user terminal processor 600 may store information about output sound corresponding to the operation information 610a in the database 610 and output the information about the output sound on the basis of the operation information 610a received from the candle controller 300, when the information about the output sound is input to the user terminal processor 600 or is selected through the input means 630, and the output sound may be stored in the user terminal 100 or provided to interface with an external system or an external server.

Through a candle warmer having mobile communication and external interface functions according to an embodiment of the present disclosure as described above, a user can be provided with a remote control configured to remotely control the candle warmer by the user and a user terminal belonging to the user of the candle warmer and having an external communication function, thereby providing convenience of use and managing usage information; an operational state and operation information can be collected and managed conveniently by a temperature sensor configured to detect temperature information and transmit collected temperature information to a candle controller and a power sensor configured to detect whether an external power source is applied; an accident due to excessive heating can be prevented using a user terminal processor configured to communicate with the user terminal and collect temperature information collected by a temperature sensor and power information collected by a power sensor by requesting a candle controller to provide the temperature information and the power information; operation information can be monitored by storing, in a database, a threshold operation time of the candle warmer, a threshold temperature, the temperature information collected by the candle controller, heating lamp operation start date and time, heating lamp operation end date and time, and power supply information; setting information additionally includes information about various types of operation modes, including an away mode, a morning mode, an afternoon mode, an evening mode, and a sleep mode, and thus, a heating time of a heating lamp and a heating time can be conveniently controlled on the basis of the various types of operation mode information; and the remote control includes a remote control inputter, a remote control signal converter and a remote control signal transmitter, and thus, information input to the remote control inputter is converted into a transmission signal by the remote control signal converter and the transmission signal is transmitted through the remote control signal transmitter and received by a remote control receiver, thereby increasing user convenience and operation stability.

While the present disclosure has been described above with respect to embodiments thereof, these embodiments are merely intended to describe examples of the technical idea of the present disclosure and it will be understood by those of ordinary skill in the art that various modifications may be made without departing from the technical idea of the present disclosure. Accordingly, the scope of the present disclosure should be interpreted based on the matters described in the claims rather than specific embodiments, and all technical ideas falling within the scope of the present disclosure should be construed as being included in the scope of the present disclosure.

REFERENCE NUMERALS

100 . . . user terminal
200 . . . remote control
210 . . . remote control inputter
210a . . . power button
210b . . . illumination button
201c . . . time button
220 . . . remote control signal converter
230 . . . remote control signal transmitter
300 . . . candle controller
310 . . . communicator
320 . . . remote control receiver
330 . . . internal timer
340 . . . memory
400 . . . temperature sensor
500 . . . power sensor
600 . . . user terminal processor
610 . . . database
610a . . . operation information
620 . . . display
630 . . . input means
631 . . . setting information
631a . . . away mode
631b . . . morning mode
631c . . . afternoon mode
631d . . . evening mode
631e . . . sleep mode
700 . . . external server
W . . . candle warmer
C . . . candle seating part
L . . . heating lamp
S1 . . . remote control signal
S2 . . . user signal

The invention claimed is:

1. A candle warmer provided to emit a scent by heating a candle using a heating lamp the candle warmer comprises:
a user terminal belonging to a user of the candle warmer and having an external communication function;
a remote control configured to interface with the candle warmer to allow the user to operate the candle warmer
a candle controller including a communicator configured to connect to the user terminal, a remote control receiver configured to interface with the remote control, and an internal timer;
a temperature sensor configured to detect temperature information and transmit collected temperature information to the candle controller;
a power sensor configured to be connected to the candle controller so as to detect whether an external power source is applied; and
a user terminal processor configured to communicate with the user terminal and request the candle controller to transmit temperature information collected by the temperature sensor and power information collected by the power sensor so as to collect the temperature information and the power information,
wherein the user terminal processor comprises a database storing operation information, a display, and an input means, wherein the operation information comprises at least a candle warmer operation threshold time, a threshold temperature, the temperature information collected by the candle controller, heating lamp operation start date and time, heating lamp operation end date and time, and power supply information.

2. The candle warmer of claim 1, wherein the user terminal processor displays details of operating the candle warmer on the display on the basis of the operation information stored in the database and according to a condition input by a user through the input means.

3. The candle warmer of claim 2, wherein the user terminal processor receives setting information through the input means and stores the setting information in the database so as to control a lamp operation time according to the temperature information collected by the temperature sensor, the setting information is transmitted to the candle controller to be stored in the memory, and the database and the memory are synchronized with each other at a certain time interval.

4. The candle warmer of claim 3, wherein the setting information further comprises information about operation modes, including at least an away mode, a morning mode, an afternoon mode, an evening mode, and a sleep mode, and the candle controller controls a heating time of a heating lamp and a heating time on the basis of time information collected by the internal timer and the information about the operation modes stored in the memory.

5. The candle warmer of claim 1, wherein the remote control further comprises a remote control inputter, a remote control signal converter, and a remote control signal transmitter, wherein information input to the remote control inputter is converted into a transmission signal by the remote control signal converter, and the transmission signal is transmitted through the remote control signal transmitter and received by the remote control receiver.

6. The candle warmer of claim 5, wherein the remote control inputter comprises an input button on a front surface of a casing of the remote control, wherein the input button comprises at least a power button, an illumination button, and a time button, wherein, when the input button is pressed, the remote control signal converter forms a digital signal corresponding to the remote control inputter, and the remote control signal transmitter transmits the digital signal, and when the digital signal is received by the remote control receiver, the candle controller ignores the setting information and preferentially controls the digital signal.

7. The candle warmer of claim 1, wherein the candle controller turns off a power source immediately when a temperature collected by the temperature sensor is greater than or equal to a threshold temperature stored in the memory and a state detected by the power sensor is a power supply state, and transmits the temperature and the threshold temperature to the user terminal processor through the communicator, and the user terminal processor displays the temperature and the threshold temperature transmitted thereto on the display.

8. The candle warmer of claim 1, wherein the candle controller stores operation time in the memory using the internal timer immediately after the candle warmer is turned on, compares the operation time stored in the memory with a set threshold time at certain time intervals, controls a power source to be turned off immediately when a total operation time exceeds the threshold time, and transmits information about collected temperatures, the threshold temperature, and the threshold time to the user terminal processor through the communicator when the power source is turned off, and the user terminal processor displays the received information on the display.

9. The candle warmer of claim 1, wherein the user terminal processor receives information about a lamp lifespan, for exchanging heating lamps, through the input means, stores the information about the lamp lifespan in the database, and displays a lamp exchange message and a total lamp operation time on the display when the lamp lifespan is over.

10. The candle warmer of claim 1, wherein the user terminal processor stores information about output sound corresponding to the operation information in the database and outputs the information about the output sound on the basis of the operation information received from the candle controller, when the information about the output sound is input to the user terminal processor or is selected through the input means, wherein the output sound is stored in the user terminal or provided to interface with an external system or an external server.

* * * * *